United States Patent
MacEachern et al.

(10) Patent No.: US 11,998,305 B2
(45) Date of Patent: Jun. 4, 2024

(54) SYSTEMS AND METHODS FOR USING A WEARABLE HEALTH MONITOR

(71) Applicant: BraveHeart Wireless Inc., Nashua, NH (US)

(72) Inventors: Stuart P. MacEachern, Hopkinton, MA (US); Martin W. Jenkel, Millbury, MA (US)

(73) Assignee: BraveHeart Wireless Inc., Nashua, NH (US)

( * ) Notice: Subject to any disclaimer, the term of this patent is extended or adjusted under 35 U.S.C. 154(b) by 503 days.

(21) Appl. No.: 17/178,886

(22) Filed: Feb. 18, 2021

(65) Prior Publication Data

US 2021/0345894 A1    Nov. 11, 2021

Related U.S. Application Data

(60) Provisional application No. 63/022,711, filed on May 11, 2020.

(51) Int. Cl.
*A61B 5/0205* (2006.01)
*A61B 5/00* (2006.01)
*G16H 80/00* (2018.01)

(52) U.S. Cl.
CPC .......... *A61B 5/02055* (2013.01); *A61B 5/002* (2013.01); *A61B 5/0022* (2013.01); *A61B 5/0024* (2013.01); *A61B 5/6802* (2013.01); *A61B 5/7264* (2013.01); *A61B 5/741* (2013.01); *A61B 5/746* (2013.01); *G16H 80/00* (2018.01); *A61B 2562/0204* (2013.01)

(58) Field of Classification Search
CPC ..... A61B 5/002; A61B 5/0022; A61B 5/6802; A61B 5/0205; A61B 5/4803; A61B 5/749
See application file for complete search history.

(56) References Cited

U.S. PATENT DOCUMENTS

| | | | |
|---|---|---|---|
| 2007/0004969 A1* | 1/2007 | Kong | A61B 5/0205 128/920 |
| 2010/0286490 A1 | 11/2010 | Koverzin | |
| 2018/0124458 A1 | 5/2018 | Konx | |
| 2018/0197624 A1 | 7/2018 | Baerenrodt et al. | |
| 2020/0337567 A1* | 10/2020 | McCalmont | G16H 40/63 |

FOREIGN PATENT DOCUMENTS

WO     20190134110 A1    7/2019

OTHER PUBLICATIONS

Extended European Search Report for Application No. 21171276.5-1113 dated Oct. 7, 2021, 11 pages.

* cited by examiner

*Primary Examiner* — Tammie K Marlen
(74) *Attorney, Agent, or Firm* — Maine Cernota & Curran

(57) ABSTRACT

A system and method for using algorithms and acoustic input to control, monitor, annotate, and configure a wearable patch that monitors physiological signals. The method comprises the receiving a transmission at a wearable device wherein the transmission can identify a mode of operation, an annotation to the data in the device, a request for data from the device, a modification of the configuration of parameters, and signals in the device.

20 Claims, 7 Drawing Sheets

SYSTEMS AND METHODS FOR USING A WEARABLE HEALTH MONITOR

RELATED APPLICATIONS

This application claims the benefit of U.S. Provisional Application No. 63/022,711, filed May 11, 2020. This application is herein incorporated by reference in its entirety for all purposes.

FIELD OF THE INVENTION

The invention relates to patient monitoring, and, more particularly, to methods and systems for using algorithms and acoustic input to control, monitor, annotate, and configure wearable health monitors that monitor physiological signals.

BACKGROUND OF THE INVENTION

The wearable medical device market has expanded greatly over the past decade, with consumer devices, such as the Fitbit® and Jawbone® wireless activity trackers, becoming a popular way for people to quantify and take charge of their personal fitness and overall well-being. While these devices are the most visible of their kind to consumers, rapid developments are simultaneously occurring in similar devices having a wide range of clinical uses. These devices are constantly becoming smaller, offering better battery life through both new battery chemistries and more efficient electronics, while providing more data and using better and more efficient algorithms to render that data useful.

As these devices become ubiquitous and more capable, they are being used to as a substitute for time consuming, expensive, and inconvenient hospital testing procedures. This transition has also allowed biometric measurements to be taken over a longer period of time, opening up new testing opportunities and new uses for the longer-term data obtained, notably by allowing for intermittent conditions to be more effectively detected, and thus treated before they become life-threatening.

In many cases an "Event Button" is used on such devices for: waking the device up; marking data in the device with a signal marking where the button was pressed; configuring the device to store data; alerting a management system that an event occurred and to take action; and labelling the data or attaching voice data to a stream of biometric data. The current use of the event button results in limited functionality, however, as it is just a button. There is no contextual information that can be associated with this event other than a manual, hand-written diary, which is used in many scenarios today.

What is needed, therefore, are techniques for efficiently utilizing the long-term data obtained from this new breed of clinical and consumer oriented devices in a way that more fully takes advantage of their capabilities and improves detection rates, especially of intermittent conditions that can be elusive during more time-limited testing and that provides more context for that data, relative to prior art devices.

SUMMARY OF THE INVENTION

A first aspect of the invention provides a method for a wearable health monitor to receive voice input from a caregiver to a patient wearing the wearable health monitor. In embodiments, this input changes the operating mode of the wearable health monitor, changes the configuration of the wearable health monitor, enables the wearable health monitor to transmit data, enables the wearable health monitor to store data, updates the wearable health monitor with new data/a new program, changes the operating mode to enhance certain physiological signals, and/or changes the operating mode to add or delete certain physiological signals.

A second aspect of the invention provides a method for a patient to command a wearable health monitor to monitor certain physiological signals. In embodiments, commands include turning on or off the wearable health monitor, adding or deleting physiological signals from a display, and/or running a physiological test using the wearable health monitor.

A third aspect of the invention provides a method for a wearable health monitor to receive voice input from a wearer. In embodiments, these commands include keywords that can be combined with the physiological data signals (herein referred to as "enriched data") such that this enriched data may be used for monitoring the patient in a more complete and better manner. This enriched data may also be used to create alarms, signal external events, create stronger and/or more individualized algorithms, trigger mechanisms for network data transmission, etc.

A fourth aspect of the invention provides a method for a wearable health monitor to analyze acoustic signals of a patient. In embodiments, acoustic signals are physiological, ambient, and/or environmental. In embodiments, this analysis includes cough analysis and/or respiratory analysis.

A fifth aspect of the invention involves the incorporation of external data, in embodiments data relating to Social Determinants of Health (SDOH), with the data generated by the device and user thereof.

In embodiments, a wearable health monitor comprises a processor, a non-transitory storage medium, a plurality of sensors, a microphone, a neural network processor and is internet-connected, either directly or through a user device. In embodiments, the wearable health monitor's connection to the internet, or cloud, is used for command and control purposes. The neural network (NN) processor is configured to interact with external entities, such as a web portal that telemedicine providers are granted access to.

In embodiments, the NN processor is configured for use as a voice interface and an inference engine running neural network models. In the case where the Neural Network Model (NNM) is running a voice application/model, embodiments include several use cases that are voice dependent and provide interaction of the device with a voice interface. The voice interface of embodiments is used to process keywords or acoustic signals. In embodiments, the NNM is used as an in-system inference engine to process biometric signals and create events and alarms based on those signals, their type(s), and conditions. In embodiments, both voice and biometric signals can be analyzed together to produce an enhanced or enriched analysis.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Smart patches, a type of wearable health sensor 500, are used in many areas of technology today. Adding voice keyword detection in place of, or in addition to, an event button 510 allows more information to be placed in a data stream that can be provided to a telemedicine provider, such as a nurse, doctor, family member of the patient, or other caregiver, providing context that allows the telemedicine provider to make more fully informed decisions, thereby improving patient outcomes. Non-limiting examples of keywords used in embodiments include faint, tired, hungry, coughing, and others.

Figure 2:
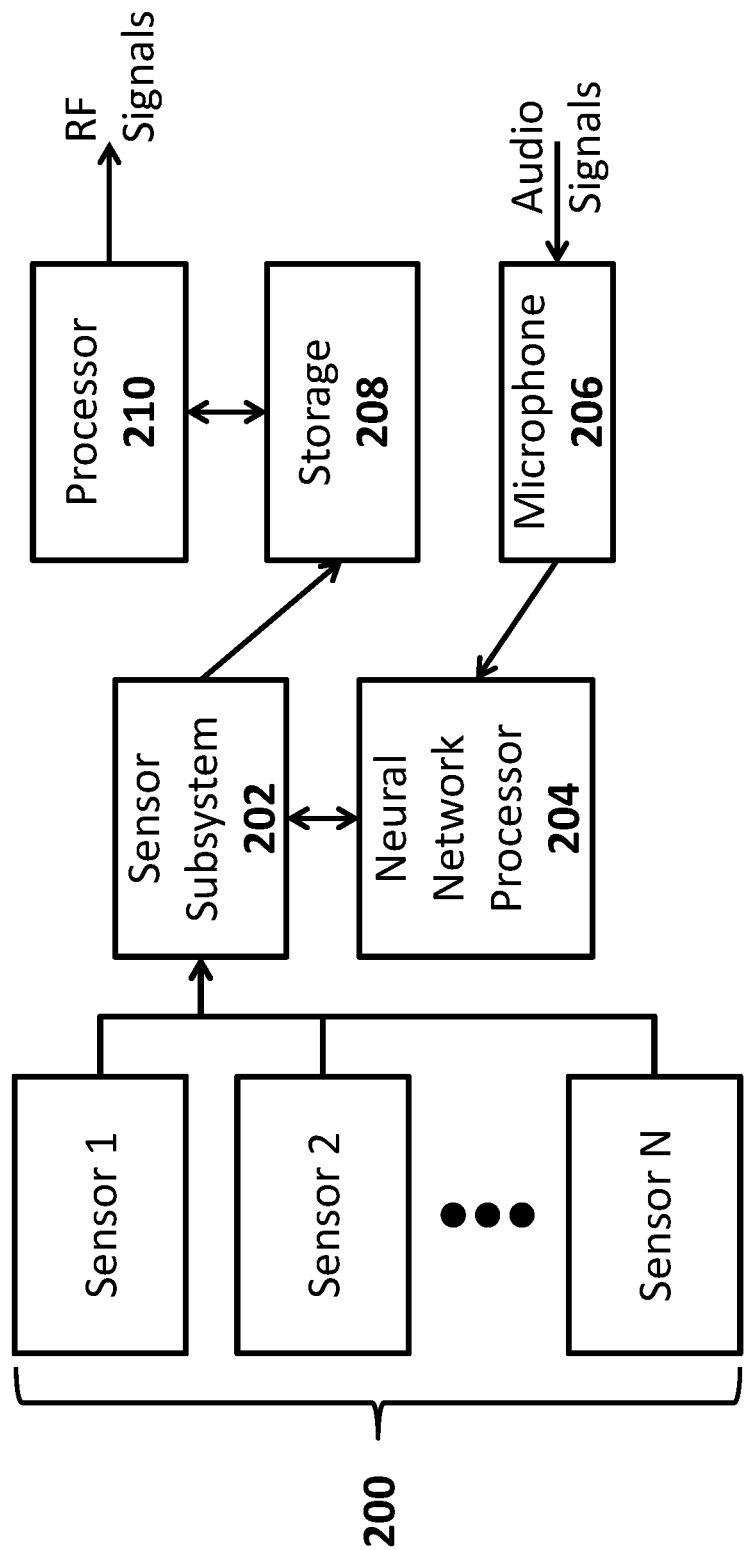
FIG. 2 is a schematic describing a wearable health monitor, in accordance with embodiments of the present disclosure.
Figure 3:
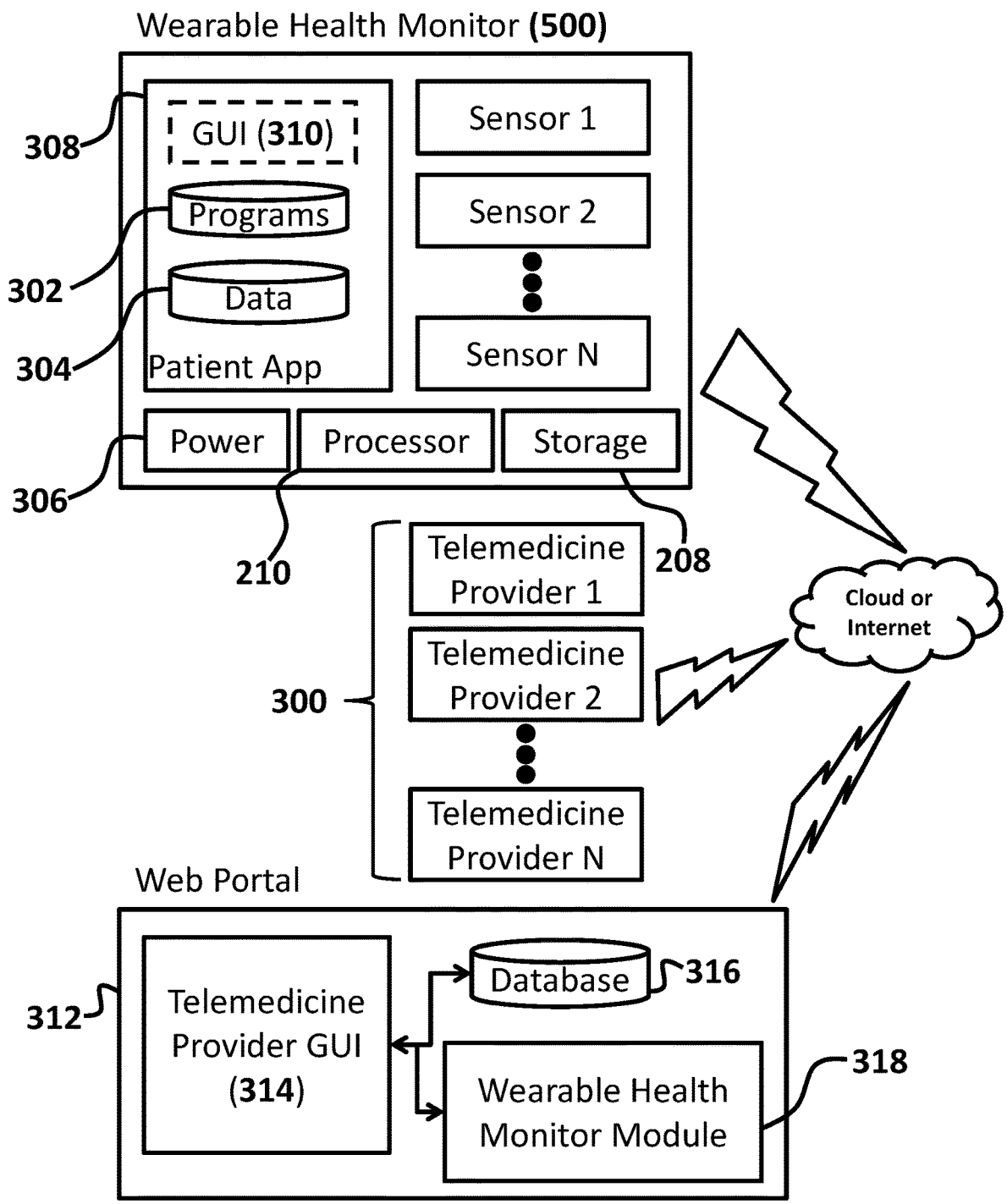
FIG. 3 is a schematic describing the internal connections of and interconnections between a wearable health monitor, patient app, and web portal used by telemedicine provider(s) to conduct telemedicine, in accordance with embodiments of the present disclosure.

High level schematics describing a wearable health monitor in accordance with embodiments of the present disclosure are shown in FIGS. 2 and 3. Referring specifically to FIG. 2, a wearable health monitor 500 is shown as including a plurality of sensors 200 in communication with a sensor subsystem 202, which is in further operative communication with a non-transitory storage 208 and processor 210 in communication with a transceiver or otherwise configured for sending and receiving RF signals. In embodiments, the sensor subsystem 202 is in further operative communication with a neural network processor 204 that is itself in further operative communication with a microphone 206, or other source of audio signals. In embodiments, the wearable health monitor 500 is configured to receive audio signals from within the vicinity of the wearable health monitor 500 through a connection with a user device, such as a Bluetooth® connection to a smartphone.

FIG. 3 provides a schematic describing the internal connections of and interconnections between a wearable health monitor 500, patient app 308, and web portal 312 used by telemedicine provider(s) to conduct telemedicine, in accordance with embodiments of the present disclosure. More specifically, the wearable health monitor 500 includes a power source 306, in embodiments a battery, a processor 210 in communication with a non-transitory storage medium 208 and a plurality of sensors 200. The wearable health monitor of embodiments further comprises a patient application 308 comprising programs 302 and data 304, which can be accessed through a GUI 310, in embodiments using a user device, such as a smartphone.

During a telemedicine session, in accordance with embodiments of the present disclosure, a telemedicine provider or providers 300 could conduct a telemedicine session through a web portal 312 comprising a telemedicine provider GUI 314 in operative communication with a database 316 and wearable health monitor module 318 configured for communication with at least one wearable health monitor 500. In embodiments, using the telemedicine provider GUI 314, the telemedicine provider is provided full or limited access to the wearable health monitor 500 and is able to reconfigure, conduct tests using, download data from, or otherwise manipulate the wearable health monitor 500 for the purposes of conducting telemedicine.

In addition, embodiments utilize groups of keywords that can be used together to provide broader context for the data together with the voice commands. These keywords are used, in embodiments, to post process or real time process the data in various ways, as described herein.

In embodiments, keywords are used to create a more concise analysis of the biometric signals and patient. For example, for a given type of physiological condition, e.g. Atrial Fibrillation (i.e. AFib), there exists a set of keywords that can be associated with the condition. These keywords, in embodiments, are faint, tired, sleepy, and similar. Such keywords, when used to enrich data, in embodiments, are associated with a specific data type. For instance, the aforementioned examples are associated with ECG data, since they would tend to provide additional insights when paired with that data type. In embodiments, different sets of keywords are associated with different sensors 200 and/or conditions being monitored. For example, embodiments associate keywords including hot, cold, shivers, chills, and similar with temperature sensors.

In embodiments, keywords are used to develop better keywords for an enhanced system as the result of building up a large diary of information of data and keywords. For example, in embodiments keywords are added and/or removed over time based on a usage model. In other embodiments, usable keywords may be modified remotely by a telemedicine provider, monitoring service, or OEM. In still further embodiments, unrecognized keywords are recorded and identified and either automatically or manually added to a list of usable keywords based on their frequency of use and/or usefulness.

In embodiments, a robust diary, a contextual record of events, is created by the wearable health sensor and made available to caregivers, telemedicine providers, and others tasked with caring for the patient or otherwise with a need to know such information. In embodiments, the diary comprises audio comprising keywords uttered by the patient to describe a physical or mental condition.

In embodiments, theses diaries, in operation, are used per application, but can also be linked and chained in sequence as the system grows in capability. Furthermore, association of keywords in the diaries linked to biometric signals and the chaining of multiple diaries is used in embodiments to obtain more complex inferences.

In embodiments, different groups of keywords are used for different applications. For example, a group of keywords is used for a specific condition, such as a heart condition, a different group of keywords is used for a patient with a respiratory condition, and a still different group of keywords is used for a diabetes condition.

In embodiments, Automatic Speech Recognition (ASR) techniques are used to transform audio data associated with speech into text representative of that speech, in embodiments using artificial intelligence, in embodiments machine learning techniques. Similarly, embodiments utilize Natural Language Understanding (NLU) to enable a wearable health sensor 500 to derive meaning from text input containing natural language. Embodiments utilize ASR and NLU together as part of a speech processing system.

In embodiments, audio is not recorded, but rather key words are identified and their use noted, thereby avoiding patient privacy issues.

Figure 1:
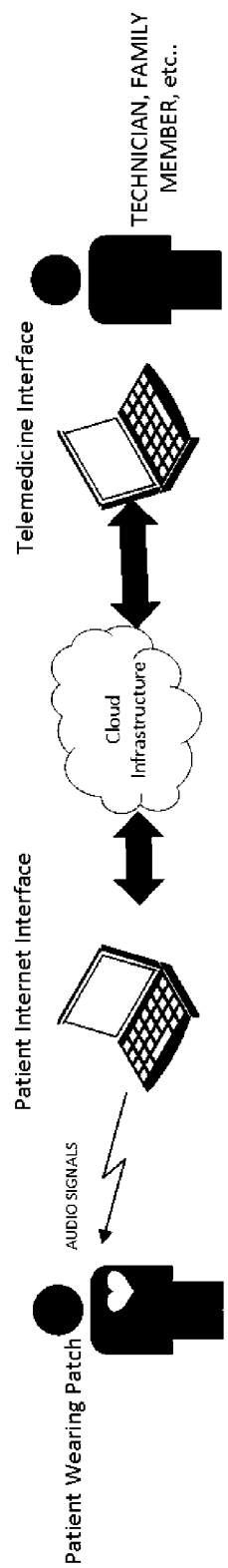
FIG. 1 is a depiction of a connection between a patient wearing a wearable health monitor and a telemedicine provider, in accordance with embodiments of the present disclosure.

To better distinguish the present invention from the prior art, an example of a patient interaction using prior art systems and methods compared to systems and methods of the present invention is now provided. More specifically, in prior art telemedicine, a caregiver would be expected to issue instructions to a patient over a communications link as shown in FIG. 1. Those instructions would typically request the patient to remotely take some action, which could be performed incorrectly. In embodiments of the present disclosure, however, a wearable health sensor 500 with a voice interface improves the interaction of the caregiver with the patient in various ways, as elaborated on below.

In a first example, a wearable health monitor 500 in accordance with embodiments of the present disclosure operates, in embodiments in a low power mode, and provides limited data at the beginning of a telemedicine session for reference by a telemedicine provider 300 (e.g. the patient's vital signs). When the caregiver enters the telemedicine session, that caregiver 300 may issue an audible keyword to enable the wearable health monitor 500 to turn on sensors and/or enable live data streams, allowing the caregiver 300 to obtain more signal details than a standard operating mode, without assistance by the patient.

In a second example, a wearable health sensor 500 in accordance with embodiments of the present disclosure allows a caregiver 300 to change a normal operating mode of the wearable health sensor 500 in various ways. For example, embodiments allow a caregiver 300 to configure the patch to store only certain signals, such as ECG data streams and individual sensors 200 or groups thereof, to enable or modify sensor 200 characteristics, to enable or disable record and playback functionality, and to run tests for specific conditions, in embodiments in preparation for a subsequent session. Of course, many other functions are also possible, as would be known to one of ordinary skill in the art.

In a third example, a telemedicine provider 300 receives an alert providing a combination of acoustic, biometric, SDOH, and/or environmental data indicative of a medical emergency and instructs the wearable health monitor 500 to dispense a dosage of medication. In embodiments, the dosage is determined algorithmically by the wearable health monitor 500, depending on the patient's biometric signals and/or verbal description of their state at the time of the issue.

In addition to interoperating with a computer, in embodiments the wearable health sensor 500 is configured to interoperate with Amazon Echo, Google Dot, Apple Siri, smartphones, and other, similar devices. In embodiments, voice processing is performed by a linked device, such as one of the aforementioned personal assistant devices.

In embodiments, an acoustic input 206 (also referred to herein as an acoustic interface 206), such as a microphone 206, is used to analyze specific patient sounds such as: coughing; respiratory noise, such as that captured by a stethoscope; acoustic heart beats; sniffling; sneezing; retching; and others, including any physiological or environmental acoustic signal that can be used as a physiological indicator.

More specifically, in embodiments, these signals are captured and analyzed in conjunction with biometric and/or environmental data from various data sources, such as such as accelerometers, peripheral capillary oxygen saturation sensors (SpO2 sensors), respiration rate sensors, galvanic skin response sensors, temperature sensors, humidity sensors, light sensors, databases, and the like. In embodiments, such sensors 200 are located on a single wearable health monitor 500 whereas, in other embodiments, such sensors 200 are spread across multiple wearable health monitors 500 or are on separate devices, such as a patient's mobile phone.

In embodiments, environmental data includes Social determinants of health (SDOH) data, i.e. data concerning the conditions in the places where people live, learn, work, and play that affect a wide range of health risks and outcomes. This information can be obtained from various databases or, in embodiments, is determined by the device itself, relying on audio, including identification of key words and association with SDOH data categories, and physiological data.

In embodiments, the wearable health sensor 500 uses an acoustic interface, in embodiments located on the wearable health sensor 500 itself, to capture sound and then uses a machine learning model running on a neural network (NN) processor 204 to process that data.

In embodiments, the NN processor 204 is used to process signals corresponding to biometric, environmental data, and/or SDOH directly and uses a NN machine learning model to draw inferences based on the machine learning models running. In embodiments, these algorithms are initiated by voice interaction. Examples of this are: afib analysis using ECG signals; motion analysis using accelerometer sensor data; blood pressure analysis using optical sensor data; and/or fever analysis using temperature sensor data.

In embodiments, algorithms are run in response to voice or system command input, which may be a command sent to the device over a network, in embodiments through an Application Programming Interface or API, a button press, or other command, as would be known to one of ordinary skill in the art.

Figure 4:
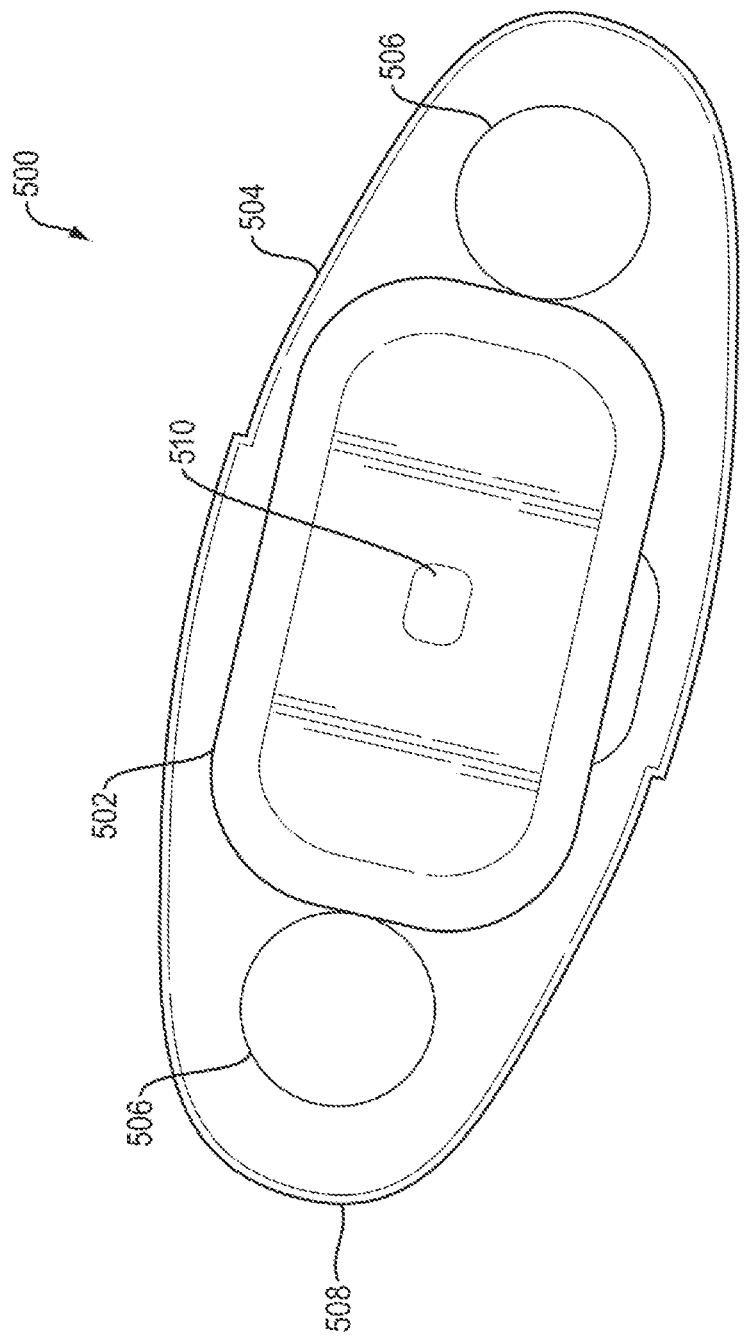
FIG. 4 is a top, elevation view of a wearable health sensor, configured in accordance with embodiments of the present disclosure.

Now referring to FIG. 4, a top, elevation view of a wearable health sensor 500, configured in accordance with embodiments of the present disclosure, is shown. The wearable health sensor 500 of embodiments includes a housing 502 containing circuitry necessary to the operation of the sensor 500. The wearable health sensor 500 further comprises a mounting strip 504, in embodiments similar in size and shape to a medium sized adhesive bandage, onto which the housing 502 can be affixed. The mounting strip 404 is used to attach the housing 502 to a user and, in embodiments, comprises an adhesive layer disposed opposite the housing 502 such that the mounting strip 504 may be removably attached to a user in any convenient location.

In embodiments, the mounting strip comprises electrodes 506 in operative communication with the housing 502, when affixed to the mounting strip 504, allowing circuitry contained therein to use the electrodes to monitor biometric data of a user therethrough.

In embodiments, the mounting strip 504 comprises a release liner 508 disposed on the adhesive portion(s) thereof, to ensure the adhesive is not contaminated prior to use.

In embodiments, the housing 502 is reusable and contains a power supply. The power supply, in embodiments, is a rechargeable battery that may be recharged using inductive charging technology, a charging port, or other charging technologies, as would be known to one of ordinary skill in the art. In other embodiments, an internal disposable battery is user-replaceable. In still other embodiments, a capacitor is used as a power source, enabling rapid charging.

In embodiments, the housing 502 comprises a function button 510, which can be programmed to perform a variety of functions, as necessary or desired. For example, the function button 510 can allow a user to identify times at which they feel symptoms of a potential arrhythmia and result in a marking of the data preceding and following the button press for review by a medical practitioner and/or for consideration by unsupervised learning algorithms.

Figure 5A:
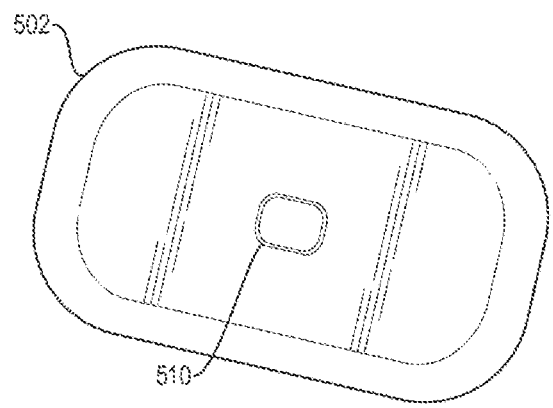
FIG. 5A is a top, elevation view of the circuitry-containing portion of a wearable health sensor, in accordance with embodiments of the present disclosure.

Now referring to FIG. 5A, a top, elevation view of the circuitry-containing portion of a wearable health sensor (also herein referred to as a smart patch) 500, in accordance with embodiments of the present disclosure, is shown.

Figure 5B:
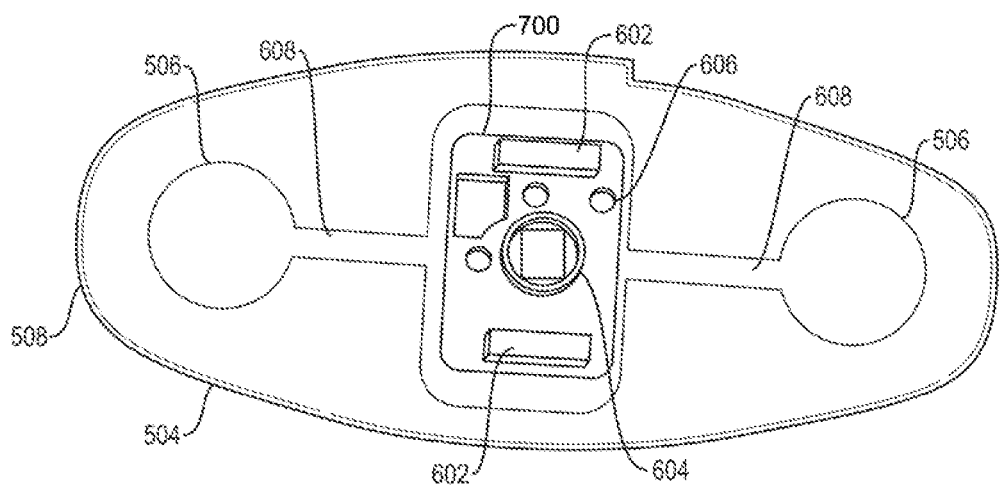
FIG. 5B is a top, elevation view of the adhesive portion of a wearable health sensor, in accordance with embodiments of the present disclosure.

FIG. 5B shows a top, elevation view of a mounting strip 504, in accordance with embodiments of the present disclosure, wherein the housing 502 has been removed therefrom. From this figure, it can be seen that the mounting strip comprises a relatively narrow spine 700 that is disposed substantially centrally on the mounting strip 504. Furthermore, the spine comprises a connector 604 disposed substantially centrally thereon. The connector 512 is configured to provide electrical connectivity between the housing 502 and mounting strip 504, which, in embodiments, contains a variety of sensors (e.g. electrodes 506) and/or pass-throughs for sensors contained within the housing 502.

For example, in embodiments, apertures 606 in the spine 600 of mounting strip 504 align with Light Emitting Diodes (LEDs) disposed on the bottom of the housing 502, allowing for the measurement of oxygen saturation in a user. In embodiments, three apertures 608 are used to enable three frequency blood oxygen saturation measurements.

In embodiments, fiber optic wires, fiber optic cables, light pipes, and/or similar light-conveying means are disposed in the mounting strip 504 and positioned to align with light-emitting elements in the housing 502. Many additional sensor types could be used in conjunction with the wearable health sensor 500 described herein, as would be known to one of ordinary skill in the art.

In embodiments, the mounting strip 504 utilizes magnets 602 to secure the housing 502 thereto, utilizing corresponding magnetic materials disposed in the housing 502. In embodiments, these magnets 602 are phased magnets 602 that act to repel the housing 502 from the mounting strip 504 if the orientation of the two is incorrect (i.e. 180° off), discouraging users from assembling the components incorrectly.

The spine 600 is, in embodiments, connected to electrodes through flexible connections 608, which may be wires, traces, or other types of flexible connections, as would be known to one of ordinary skill in the art.

Figure 6A:
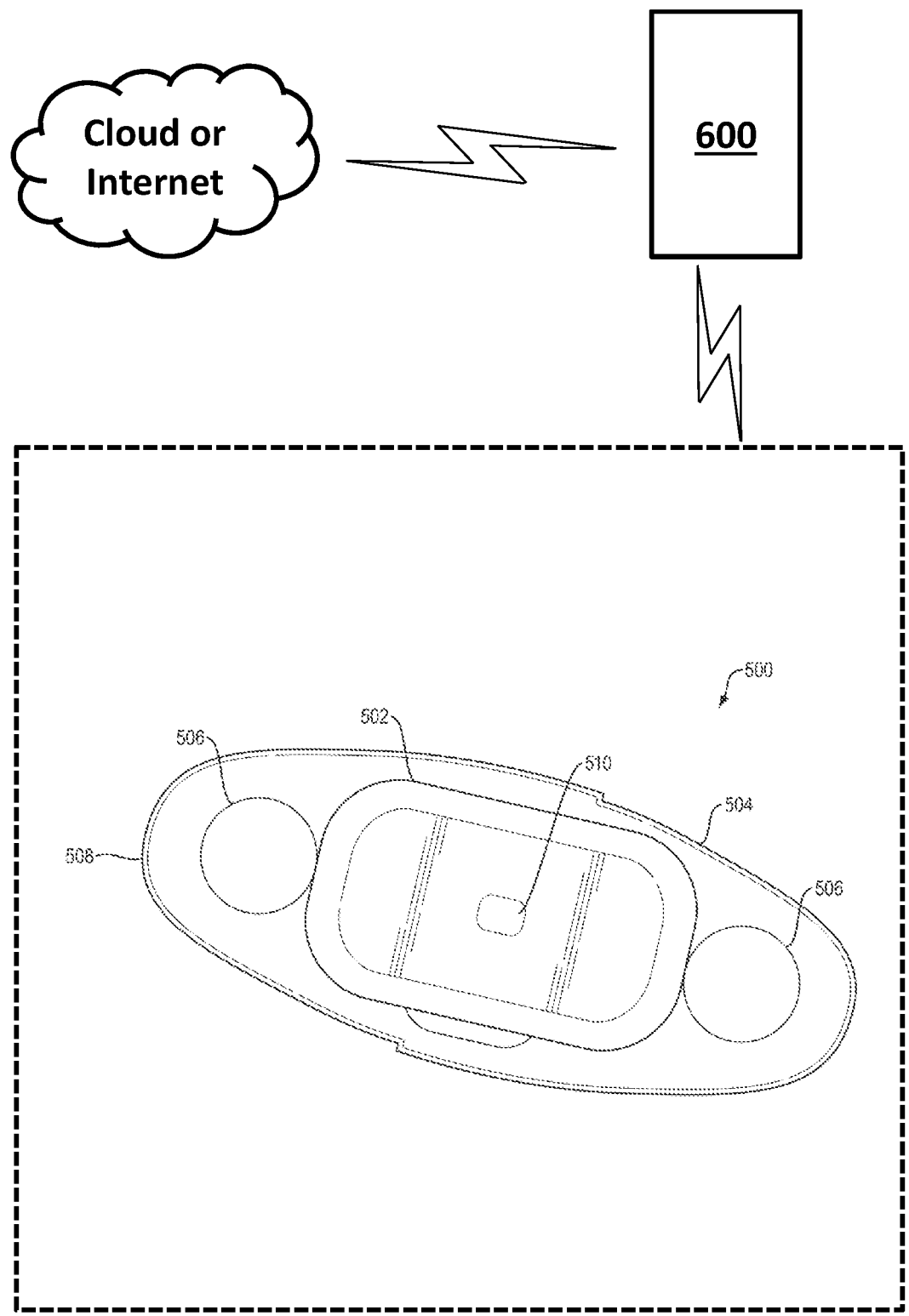
FIG. 6A is a depiction of a wearable health sensor in operative communication with a network, through a patient internet interface, in accordance with embodiments of the present disclosure.

Now referring to FIG. 6A, wearable health sensor 500 is shown in operative communication with a network-enabled device 700, which may, in embodiments, be in further communication with a network 702. In embodiments, this network 702 may be a local-area network, such as might be used in a hospital setting for intra-hospital communications, while in other embodiments this network 702 may be a wide-area network, such as the internet.

Figure 6B:
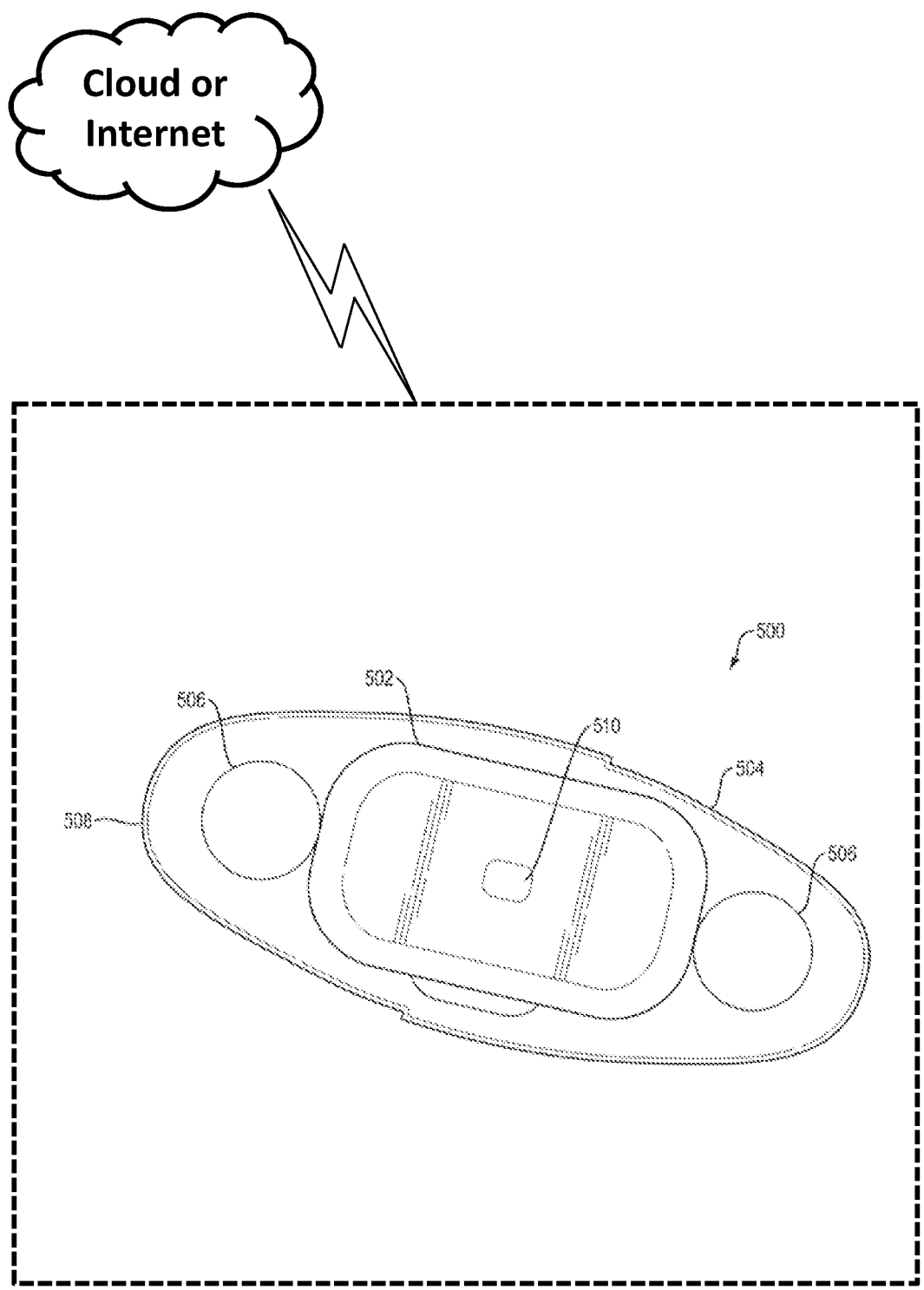
FIG. 6B is a depiction of a wearable health sensor in operative communication with a network, in accordance with embodiments of the present disclosure.

Now referring to FIG. 6B, a wearable health sensor 500 is shown in operative communication directly with a network 702, in accordance with embodiments of the present disclosure.

Communications between wearable health sensors 500 and networks (e.g. private cloud or internet), directly, in embodiments, are enabled in a variety of ways, such as by the inclusion of a cellular data-capable modem and/or a WiFi enabled chipset in the wearable health sensor 500, although other methods of enabling network access would be known to one of ordinary skill in the art.

In embodiments, the network-enabled device 600 is a user device, such as a cellular phone with a data connection (e.g. to the internet) or a personal computer. In embodiments, the wearable health sensor 500 connects to the network-enabled device 600 using Bluetooth®, or, more preferably, Bluetooth Low Energy® while, in other embodiments, a connection is made using zigbee, zwave, 802.11x, or other network protocols, as would be known to one of ordinary skill in the art.

In embodiments, communication between wearable health sensors 500 may be enabled via Bluetooth®, WiFi, cellular data, or a number of other means, which would be known to one of ordinary skill in the art.

Embodiments may further employ noise cancellation for multi-sensor 500 environments. In embodiments, noise cancellation may be achieved through the use of a wideband noise sensor, which is used to provide a measure of the background noise, combined with noise-cancelling algorithms. In some embodiments, five wearable health sensors 500 may be used to provide reverse phase noise cancellation capabilities.

Still even other embodiments group multiple 3-lead wearable health sensors 500, allowing the system to perform as a 6 or 12 lead ECG.

In embodiments, detection types include heart rate and heart rate variability, steps taken, respiratory rate, blood oxygen levels, skin temperature, body posture, glucose levels, fall detection, and GSR/EDA detection (change in amount of sweat in sweat glands).

The foregoing description of the embodiments of the invention has been presented for the purposes of illustration and description. Each and every page of this submission, and all contents thereon, however characterized, identified, or numbered, is considered a substantive part of this application for all purposes, irrespective of form or placement within the application. This specification is not intended to be exhaustive or to limit the invention to the precise form disclosed. Many modifications and variations are possible in light of this disclosure.

What is claimed is:

1. A wearable health monitor comprising:
   a processor in operative communication with a non-transitory storage medium;
   at least one biometric sensor configured to measure at least one biometric signal, the at least one sensor being in operative communication with said processor;
   and at least one audio source in operative communication with said processor,
   wherein the wearable health monitor is configured to store biometric data from said at least one biometric sensor,
   wherein the wearable health monitor is further configured to store a contextual record of events comprising predetermined keywords uttered by a patient, picked up by the at least one audio source, and recognized as keywords by the wearable health monitor, those keywords being descriptive of a physical or mental condition affecting the patient,
   wherein the utterance of a predetermined keyword is configured to trigger the keyword and biometric data to be written to the contextual record of events, and
   wherein the contextual record of events includes timestamp data specifically identifying a time at which a predetermined keyword was uttered as well as the time biometric data was measured, allowing for the correlation of biometric data and predetermined keywords.

2. The wearable health monitor of claim 1 wherein biometric data further includes physiological and/or environmental acoustic data picked up by said at least one audio source.

3. The wearable health monitor of claim 1 wherein said at least one audio source is a microphone.

4. The wearable health monitor of claim 1 wherein said at least one audio source is a network-connected user device comprising a microphone in operative communication with the wearable health sensor.

5. The wearable health monitor of claim 4 further comprising a connection module configured to wirelessly connect said wearable health monitor to a wireless network.

6. The wearable health monitor of claim 1 wherein said connection module is configured to allow said wearable health monitor to connect to a user device.

7. The wearable health monitor of claim 6 wherein said user device is a cellular phone.

8. The wearable health monitor of claim 4 wherein said wearable health monitor is configured to monitor heart rate, heart rate variability, steps taken, respiratory rate, blood oxygen levels, skin temperature, body posture, and galvanic skin response/electro dermal activity.

9. The wearable health monitor of claim 1 further comprising an emergency function configured to perform a function selected from the group consisting of record data, alert emergency responders, and mark the data being recorded at that time for later review, the emergency function being configured for activation by a neural network processor configured to process signals corresponding to biometric and acoustic data obtained by the wearable health monitor and to apply a machine learning model thereto to determine an appropriate action to take.

10. The wearable health monitor of claim 1 wherein the wearable health monitor is further configured to store a contextual record of events comprising social determinant of health data and wherein the contextual record of events, biometric data, and social determinant of health data each include timestamps, allowing for their correlation.

11. The wearable health monitor of claim 10 wherein the social determinant of health data is determined using a remote database via a network connection.

12. The wearable health monitor of claim 10 wherein the social determinant of health data is determined using keywords picked up by the at least one audio source and/or biometric data determined by the at least one biometric sensor.

13. The wearable health monitor of claim 1 wherein the wearable health monitor is configured to accept voice commands and said voice commands are configured to allow a user or caregiver to perform a function selected from the group consisting of: configure the wearable health monitor to store data from only certain sensors or of certain types, to enable or modify sensor characteristics, to enable or disable record and playback functionality, to run tests for specific conditions, create alarms, signal external events, and trigger mechanisms for data transmission.

14. The wearable health monitor of claim 1 further comprising a neural network processor configured to process signals corresponding to biometric and acoustic data obtained by the wearable health monitor, and to apply a machine learning model to draw inferences thereon.

15. The wearable health monitor of claim 14 wherein the application of a machine learning model to data is initiated by voice command.

16. The wearable health monitor of claim 1, wherein keywords are identified and their use noted in the contextual record without storing any associated audio.

17. The wearable health monitor of claim 1, wherein predetermined keywords are configured to initiate real time processing of the biometric data.

18. The wearable health monitor of claim 1, wherein predetermined keywords are configured to trigger post-processing of the biometric data.

19. A method of monitoring biometric data in a patient comprising:
at a first location:
providing a network-connected, wearable health monitor configured to accept voice commands and comprising at least one acoustic input and at least one biometric sensor;
attaching the wearable health monitor to a patient;
at a second location:
having a telemedicine provider initiate a telemedicine session comprising at least bidirectional audio with the patient; and
the telemedicine provider manipulating the wearable health monitor using voice commands.

20. The method of monitoring biometric data in a patient of claim 19 wherein said voice commands are configured to allow a user or caregiver to perform a function selected from the group consisting of: configure the wearable health monitor to store data from only certain sensors or of certain types, enable or modify sensor characteristics, enable or disable record and playback functionality, run tests for specific conditions, create alarms, signal external events, and trigger mechanisms for data transmission.

* * * * *